US006855330B2

(12) United States Patent
Sirinyan et al.

(10) Patent No.: US 6,855,330 B2
(45) Date of Patent: Feb. 15, 2005

(54) INSECTICIDE SUSPENSION CONCENTRATES

(75) Inventors: Kirkor Sirinyan, Bergisch Gladbach (DE); Thomas Böcker, Leichlingen (DE); Klaus Mrusek, Bergisch Gladbach (DE); Ulrike Schneider, Langenfeld (DE); Rainer Sonneck, Leverkusen (DE)

(73) Assignee: Bayer Aktiengesellschaft, Leverkusen (DE)

( * ) Notice: Subject to any disclaimer, the term of this patent is extended or adjusted under 35 U.S.C. 154(b) by 94 days.

(21) Appl. No.: 09/155,849

(22) PCT Filed: Mar. 27, 1997

(86) PCT No.: PCT/EP97/01568

§ 371 (c)(1),
(2), (4) Date: Oct. 2, 1998

(87) PCT Pub. No.: WO97/37538

PCT Pub. Date: Oct. 16, 1997

(65) Prior Publication Data

US 2003/0229139 A1 Dec. 11, 2003

(30) Foreign Application Priority Data

Apr. 9, 1996 (DE) .......................................... 196 13 974

(51) Int. Cl.[7] .............................................. A01N 25/26
(52) U.S. Cl. ........................ 424/421; 424/405; 424/406; 514/531
(58) Field of Search ................................ 424/405, 409, 424/417–420, 489–498, 421; 514/531, 770, 521

(56) References Cited

U.S. PATENT DOCUMENTS 4,155,314 A  5/1979  O'Callaghan et al. .......... 111/1
4,678,774 A  7/1987  Putter et al. .................... 514/30
4,804,399 A  2/1989  Albrecht et al. ................ 71/93
5,110,594 A  5/1992  Morita ......................... 424/405
5,516,529 A  5/1996  Zellweger .................... 424/466

FOREIGN PATENT DOCUMENTS

| DE | 837243 | 4/1952 |
| EP | 0 029 626 | 3/1983 |
| EP | 0659341 A1 * | 6/1995 |
| ES | 2022016 | 11/1991 |
| GB | 1173027 | 12/1969 |
| JP | 1-279802 | 11/1989 |
| WO | 95/15146 | 6/1995 |
| WO | 95/26631 | 10/1995 |
| WO | 96/25850 | 8/1996 |

OTHER PUBLICATIONS

CAS Registry File: beta cyfluthrin & cyfluthrin 1967.*
Database WPI, Sec. Ch, An 93–232211 and JP 05 155 706 A (Nippon Soda Co.) Jun. 22, 1993.
Chemical Abstracts Vo. 102, No. 25, Jun. 24, 1985, Abstract No. 216909 & JP 60 013 701 A (Sumitomo).
Database WPI, Sec. Ch, an 89–359856 & JP 01 268 604 A (Kumiai Chem Ind Co Ltd) Oct. 26, 1989.
Database WPI, Sec. Ch, An 89–359856 & JP 01 258 603 A (Kumiai Chem Ind Co Ltd) Oct. 16, 1989.
Database WPI, Sec. Ch, an 83–750620 & JP 58 124 703 A (Sumitomo Chem Co Ltd) Jul. 25, 1983.

* cited by examiner

*Primary Examiner*—Neil S. Levy
(74) *Attorney, Agent, or Firm*—Richard E. L. Henderson; Raymond J. Harmuth

(57) ABSTRACT

Disclosed herein is an aqueous suspension of insecticidally active compounds comprising a solid active compound applied as a coating to an inorganic carrier and auxiliaries, water and glycerol.

2 Claims, No Drawings

INSECTICIDE SUSPENSION CONCENTRATES

This application is the national stage of PCT/EP97/01568 filed Mar. 27, 1997, which in turn claims priority of German Application Serial No. 196-13-974.0 filed Apr. 9, 1996.

The present invention relates to novel aqueous suspensions of insecticidally active compounds.

When using sparingly water-soluble active compounds in the form of water-diluted sprays, it is necessary to prepare water-suspendable formulations of these active compounds. For this purpose, the active compounds are ground and mixed with emulsifiers, dispersants and optionally other additives. The preparation of such formulations is described for example in DE 28 11 828 and DE 32 40 862.

$TiO_2$, $Al_2O_3$ and $SiO_2$ are known to be used as formulation auxiliaries in the preparation of insecticidal formulations. U.S. Pat. No. 5,110,594, for example, describes the use of $Al_2O_3$ for preparing insecticide-comprising impregnated paper coatings. $TiO_2$-comprising insecticidal coatings are described in the Application ES-A 20 22 016.

$Al_2O_3$-comprising formulations of solids are described in EP-A 391 851.

$Al_2O_3$-comprising insecticidal suspensions are described in JP 01268604 and JP 01258603.

The oxides employed in these formulations improve essentially the physical properties, such as film forming or suspension stability, of the formulation.

Chlorpyrifos-impregnated $Al_2O_3/SiO_2$ carriers employed for preparing powder formulations are described in JP 01279802. This measure is said to achieve better application through formation of a dust.

The present invention relates to aqueous suspensions of insecticidal active compounds, characterized in that they comprise:

a) 0.1 to 12.5% of an inorganic carrier having a particle size of 1 to 30 µm and bearing a coating of active compound, b) 2.5 to 10% of formulation auxiliaries, c) 62.5 to 97.4% of water d) 0 to 15% of glycerol (the percentages are % by weight).

The formulations according to the invention are outstandingly suitable for preparing spray liquids for professional use in pest control in the household, in industry, in buildings for livestock, etc. They have excellent storage stability and very good dispersability in water. In addition, they can be produced at an economical price. The solvents selected do not cause any problems for the user.

Preferred active compounds are insecticides used in the hygiene sector and in professional pest control, such as carbamates, pyrethroids, phosphoric esters, and mixtures of these active compounds with synergists.

Suitable carbamates are substituted phenyl and naphthyl carbamates.

Preference is given to:
2-isobutylphenyl methylcarbamate,
4-dimethylamino-3-methyl-phenyl methylcarbamate,
2-isopropoxy-phenyl methylcarbamate,
1-naphthyl methylcarbamate,
m-tolyl methylcarbamate,
3,4-xylyl methylcarbamate,
3,5-xylyl methylcarbamate,
2-[1,3-dioxolan-2-yl]-phenyl methylcarbamate.

Preferred pyrethroids are the compounds with the common names permethrin, cypermethrin, deltamethrin, cyfluthrin and β-cyfluthrin.

Preferred phosphoric esters are the compounds with the common names fenitrothion and trichlorfon.

A preferred synergist for these compounds is piperonyl butoxide.

Particularly preferred active compounds are pyrethroids. A very particularly preferred pyrethroid is β-cyfluthrin.

Inorganic carriers are $TiO_2$, $Al_2O_3$, MgO and $SiO_2$ or their mixtures with one another.

A particularly preferred carrier is $Al_2O_3$.

The active compounds applied to an inorganic carrier are present at 0.1 to 12.5%, preferably at 0.1 to 7.5%, particularly preferably at 0.1 to 5%. The formulation may additionally comprise: free solid active compound at a concentration of 0.1 to 12.5%, preferably 0.1 to 7.5%, particularly preferably 0.1 to 5%. Free active compound may be present depending on the conditions of manufacture, for example as a result of abrasion. The amount of active compound applied to carriers and of free active compound may vary significantly with respect to each other.

The mean particle size of the carrier to which active compound has been applied, for example of $Al_2O_3$ or $TiO_2$, is from 1.0 to 30.0 µm, preferably 5.0 to 25.0 µm, particularly preferably 6.0 to 15.0 µm.

The carrier/active compound system may be of symmetrical spherical or asymmetrical shape. Its particle size is determined by known analytical methods, such as screen analysis.

The coating of the carriers with active compound can be achieved by customary coating processes, such as dipping or spraying and subsequent evaporation of the solvent. The active-compound-coated carrier can then optionally be mixed with additional finely ground active compound and homogenized.

Another option is the in situ preparation of a mixture comprising active-compound-coated carrier and free, finely pulverulent active compound. The preparation of such systems may be controlled in a known manner by varying the concentration of the active compound solution, or the evaporation rate of the solvent, etc.

Additionally, the formulations according to the invention may comprise customary auxiliaries such as emulsifiers, stabilizers, preservatives, antioxidants or odorants.

Suitable emulsifiers are: non-ionic surfactants, for example polyoxyethylated castor oil, polyoxyethylated sorbitan monooleate, sorbitan monostearate, glycerol monostearate, polyoxyethylene stearate, alkylphenyl polyglycol ether, for example according to U.S. Pat. No. 3,948,636 or British Patent Specification 148 010; anionic surfactants, such as sodium lauryl sulfate, fatty alcohol ether sulfates, the monoethanolamine salts of mono/dialkyl polyglycol ether orthophosphoric acid esters and the alkali metal salts of sulfosuccinic acid, for example according to DE 32 40 862; cationic surfactants such as cetyltrimethylammonium chloride, and ampholytic surfactants, such as disodium N-lauryl-β-imino-dipropionate or lecithin.

Suitable stabilizers and antioxidants are sulfites or metabisulfites, such as potassium metabisulfite, organic acids, such as citric acid and ascorbic acid, inorganic acids, such as hydrochloric acid or sulfuric acid, and phenols, such as butylhydroxytoluene, butylhydroxyanisole and tocopherol.

Suitable preservatives are formaldehydes or formaldehyde-releasing agents and derivatives of benzoic acid, such as, for example, p-hydroxybenzoic acid.

Other suitable auxiliaries are: defoamers based on polysiloxane and thickeners based on polysaccharide.

The auxiliaries mentioned may be present in the formulations according to the invention in concentrations by weight of 2.5 to 10%.

The amount of glycerol is from 0 to 15%, particularly preferably 7.5 to 12.5%. The compositions according to the invention are applied simply by diluting the suspension concentrates with the desired amount of water, brief stirring and application to walls etc.

The novel suspension concentrates exhibit outstanding sediment stability.

The invention is illustrated by the examples below.

EXAMPLE 1

| | |
|---|---|
| 11.8 g | of β-cyfluthrin-coated Al$_2$O$_3$ (1) and free active compound |
| 3.0 g | of emulsifier 373 tri(methylstyryl)phenol ethoxylate (29 EO) |
| 11.6 g | of glycerol |
| 0.36 g | of gum xanthan (a high-molecular-weight polysaccharide) |
| 0.025 g | of 96% strength sulfuric acid, technical |
| 0.1 g | of acrylmethanol mono-hemiformal |
| 73.1 g | of deionized water |

(1) Preparation 125.0 g of β-cyfluthrin are dissolved in 2,000 ml of acetone and mixed with Al$_2$O$_3$ of a particle size of 4.8 to 22.5 μm, and the acetone is distilled off at 54° C. under N$_2$. β-Cyfluthrin-coated Al$_2$O$_3$ carriers are obtained. The amount of free, uncoated active compound is about 20%. The mean particle size of the free, uncoated active compound is about 11 μm.

EXAMPLE 2

| | |
|---|---|
| 11.8 g | of β-cyfluthrin-coated Al$_2$O$_3$ (2) and free active compound |
| 3.0 g | of baykanol SL (a condensate of a 1- to 2-times sulfonated diaryl ether isomer mixture, Bayer AG) |
| 1.0 g | of baysilon-E (a silicone-containing defoamer, Bayer AG) |
| 3.5 g | of neutral emulsifier based on ethylene oxide and propylene oxide (MW~6,000 g/mol) |
| 0.5 g | of gum xanthan (a high-molecular-weight polysaccharide) |
| 0.025 g | of 96% strength sulfuric acid, technical |
| 80.175 g | of deionized water |

(2) Preparation 125.0 g of β-cyfluthrin are dissolved in 1,750 ml of acetone and mixed with Al2O$_3$ of a particle size of 4 to 28 μm, and the acetone is distilled off at 54° C. under N$_2$.

β-Cyfluthrin-coated Al$_2$O$_3$ carriers are obtained. The amount of free, uncoated active compound is about 30%.

The particle size of the free, uncoated active compound is about 6 μm.

COMPARATIVE EXAMPLE

| | |
|---|---|
| 11.8 g | of β-cyfluthrin having a mean particle size of ~4 μm |
| 3.0 g | of emulsifier 373 |
| 11.6 g | of glycerol |
| 0.36 g | of gum xanthan |
| 0.025 g | of 96% strength sulfuric acid, technical |
| 0.1 g | of acrylmethanol mono-hemiformal |
| 73.1 g | of deionized water |

EXAMPLE A

Test for Residual Action
Test Method
Formulation:
  SC=suspension concentrate.
Surfaces:
  PVC (Tarket spezial, light green, Article No. 657.427.52), painted plywood (paint: Herbol Malerqualität white, 301 RAL 9010), unglazed tiles (Villeroy und Boch, Art. 2103, Col. 435, Nuance 558), (Size: 15×15 cm=225 cm$^2$)

Test:

Blattella germanica L 5, Blatta orientalis L 5

Treatment of the surfaces:

Spraying of the surfaces is carried out in a fume cupboard allowing regulation of the air flow in such a way that the spray is not affected. The formulations are dissolved in tap water. Spraying is carried out using a glass nozzle and an air pressure of 0.1 bar from a distance of 13 cm. The application rate is 2.5 cm$^3$/surface, which, minus the overspray, corresponds to a spray quantity of 100 cm$^3$/m$^2$.

Animal Material and Evaluation:

In each case, 5 test animals are kept on the surfaces within talcumed glass rings (diameter 9.4 cm, height 5.5 cm). One day after treatment and after 1, 2, 3, 4, 6 and 8 weeks and further at four-week intervals, the animals are placed on the surfaces and remain exposed there in each case for 24 hours.

Evaluation was carried out by % knock down after 15, 30 and 60 minutes, and then after 2, 3, 4, 5, 6 and 8 hours. After 24 hours, the destruction in percent is determined and the animals are taken off the surfaces.

Residual action of β-cyfluthrin of various formulations on various surfaces.

| | | Application | 100% mortality within 24 hours until weeks | | |
|---|---|---|---|---|---|
| Test animals | Formulation | rate mg a.i./m$^2$ | PVC | painted wood | unglazed tiles |
| Blattella germanica 5th larvae stage | Example 1 | 5.0 | 6 | 16 | 12 |
| | Comparative example | 7.5 | 8 | 20 | 12 |
| | | 10.0 | 12 | >28 | 24 |
| | | 10.0 | 4 | 20 | 12 |
| Blatta orientalis 5th larvae stage | Example 1 | 5.0 | 6 | 12 | >28 |
| | | 7.5 | 12 | 24 | >28 |
| | | 10.0 | 20 | 24 | >28 |
| | Comparative example | 10.0 | 6 | 12 | >28 |

Residual action of β-cyfluthrin of various formulations on various surfaces.

| | | Application | 100% mortality within 24 hours until weeks | | |
|---|---|---|---|---|---|
| Test animals | Formulation | rate mg a.i./m$^2$ | PVC | painted wood | unglazed tiles |
| Blattella germanica 5th larvae stage | Example 2 | 5.0 | 6 | 16 | 12 |
| | Comparative example | 7.5 | 8 | 20 | 12 |
| | | 10.0 | 12 | >28 | 24 |
| | | 10.0 | 4 | 20 | 12 |
| Blatta orientalis 5th larvae stage | Example 2 | 5.0 | 6 | 12 | >28 |
| | | 7.5 | 12 | 24 | >28 |
| | | 10.0 | 20 | 24 | >28 |
| | Comparative example | 10.0 | 6 | 12 | >28 |

What is claimed is:

1. An aqueous suspension of insecticidal active compounds comprising:
   a) 0.1 to 12.5% of an inorganic carrier having a particle size of 1 to 30 μm bearing a coating of beta-cyfluthrin thereon,
   b) 2.5 to 10% formulation auxiliaries,
   c) 62.5 to 97.4% of water,
   d) 0 to 15% of glycerol, and
   e) free solid beta-cyfluthrin at a concentration of 0.1 to 30% wherein the percentages are % by weight of the suspension.

2. The aqueous suspension of claim 1 wherein the inorganic carrier is selected from the group consisting of MgO, $TiO_2$, $SiO_2$, $Al_2O_3$, and mixtures thereof.

* * * * *